United States Patent
Zaima et al.

(10) Patent No.: US 10,322,013 B2
(45) Date of Patent: Jun. 18, 2019

(54) MEASURING INSTRUMENT FOR USE IN ARTIFICIAL KNEE JOINT REPLACEMENT SURGERY

(71) Applicant: KYOCERA Medical Corporation, Osaka-shi, Osaka (JP)

(72) Inventors: Hironori Zaima, Osaka (JP); Masahiko Hashida, Osaka (JP)

(73) Assignee: KYOCERA CORPORATION, Kyoto (JP)

( * ) Notice: Subject to any disclaimer, the term of this patent is extended or adjusted under 35 U.S.C. 154(b) by 106 days.

(21) Appl. No.: 15/118,919

(22) PCT Filed: Feb. 20, 2015

(86) PCT No.: PCT/JP2015/054762
§ 371 (c)(1),
(2) Date: Aug. 15, 2016

(87) PCT Pub. No.: WO2015/129573
PCT Pub. Date: Sep. 3, 2015

(65) Prior Publication Data
US 2016/0367382 A1  Dec. 22, 2016

(30) Foreign Application Priority Data
Feb. 28, 2014 (JP) ................................ 2014-039704

(51) Int. Cl.
*A61F 2/46* (2006.01)
*A61B 17/15* (2006.01)
(Continued)

(52) U.S. Cl.
CPC .......... *A61F 2/4657* (2013.01); *A61B 5/1121* (2013.01); *A61B 5/4528* (2013.01);
(Continued)

(58) Field of Classification Search
CPC .......... A61F 2/46; A61F 2/4657; A61F 2/461; A61B 17/15; A61B 17/154
See application file for complete search history.

(56) References Cited

U.S. PATENT DOCUMENTS 5,606,590 A * 2/1997 Petersen .................. A61B 6/08
378/177
5,611,353 A  3/1997 Dance et al.
(Continued)

FOREIGN PATENT DOCUMENTS

JP  09-500550 A   1/1997
JP  2002-519093 A  7/2002
(Continued)

OTHER PUBLICATIONS

International Search Report, PCT/JP2015/054762, dated May 19, 2015, 2 pgs.

*Primary Examiner* — Christopher J Beccia
(74) *Attorney, Agent, or Firm* — Volpe and Koenig, P.C.

(57) ABSTRACT

Provided is a measuring instrument for use in artificial knee joint replacement surgery that can perform knee joint alignment measurement more accurately. A measuring instrument for use in artificial knee joint replacement surgery includes a guide section. The guide section is used to indicate, from the outside of a patient, the position of a femoral head center of a hip joint of the patient. The guide section indicates the position of the femoral head center while being arranged based on preliminarily measured relative positions of an anterior superior iliac spine and the femoral head center of the patient. The anterior superior iliac spine is viewable from the outside of the patient.

7 Claims, 15 Drawing Sheets

(51) Int. Cl.
  *A61B 5/11* (2006.01)
  *A61B 5/00* (2006.01)
  *A61F 2/38* (2006.01)

(52) U.S. Cl.
  CPC ............ *A61B 17/154* (2013.01); *A61F 2/461* (2013.01); *A61F 2/38* (2013.01); *A61F 2002/4668* (2013.01)

(56) References Cited

U.S. PATENT DOCUMENTS

| | | |
|---|---|---|
| 6,554,837 B1 | 4/2003 | Hauri et al. |
| 8,672,862 B2 | 3/2014 | Kanekasu |
| 2009/0076507 A1 | 3/2009 | Claypool et al. |
| 2011/0103556 A1* | 5/2011 | Carn ................ A61B 6/12 |
| | | 378/205 |
| 2012/0029581 A1* | 2/2012 | Kanekasu ............ A61B 90/06 |
| | | 606/86 R |

FOREIGN PATENT DOCUMENTS

| | | |
|---|---|---|
| JP | 2008-125706 A | 6/2008 |
| JP | 2012-029769 A | 2/2012 |
| JP | 3183614 U | 5/2013 |

* cited by examiner

Example of flow of treatment regarding
artificial knee joint replacement surgery Example of flow of preoperative examination Example of alignment measurement procedure Another example of alignment measurement procedure

MEASURING INSTRUMENT FOR USE IN ARTIFICIAL KNEE JOINT REPLACEMENT SURGERY

TECHNICAL FIELD

The present invention relates to a measuring instrument for use in artificial knee joint replacement surgery, which is used in surgery for replacing a knee joint of a patient with an artificial knee joint.

BACKGROUND ART

In artificial knee joint replacement surgery, a femoral component is fixed to the distal part of a femur of a patient, and a tibial component is fixed to the proximal part of a tibia of the patient. The femoral component has a convex surface, which is received by a concave surface of the tibial component. With this configuration, when the patient bends and extends the knee, the femoral component and the tibial component slide relative to each other while being in contact with each other, achieving smooth movement of the knee of the patient.

In the artificial knee joint replacement surgery, osteotomy is performed on the distal part of the femur. With this, the distal part of the femur is formed into a shape appropriate for installation of the femoral component. Furthermore, in the artificial knee joint replacement surgery, osteotomy is performed on the proximal part of the tibia. With this, the proximal part of the tibia is formed into a shape appropriate for installation of the tibial component. Various instruments are known as instruments for use in osteotomy (see Patent Documents 1 and 2, for example).

Also, the arrangement of the femoral component at the distal part depends on the orientation (angle) and the like of the section of the distal part to which the femoral component is to be fixed. Similarly, the arrangement of the tibial component at the proximal part depends on the orientation (angle) and the like of the section of the proximal part to which the tibial component is to be fixed. Also, the movable range of the knee joint in its bending motion, extending motion, medial/lateral rotation, and varus/valgus motion depends on the arrangement of the femoral component and the tibial component, and the like.

CITATION LIST

Patent Documents

Patent Document 1: JP 2008-125706A
Patent Document 2: JP 3183614Y

DISCLOSURE OF THE INVENTION

Problem to be Solved by the Invention

In artificial knee joint replacement surgery, the position of the knee joint center may be set on a straight line connecting the position of the hip joint center and the position of the foot joint (ankle joint) center of the patient. When such a layout is employed, a surgeon uses, for example, a measuring instrument to check whether or not the position of the knee joint center (alignment) is positioned on the straight line. More specifically, the measuring instrument includes a plate and a metal bar. The plate is flat-shaped, and is arranged between the distal part and the proximal part that were subjected to osteotomy. The plate has a projecting part. This projecting part has a through-hole. The metal bar, which has a length of about 1 m, passes through the through-hole. The metal bar is arranged so as to pass through the hip joint center and the foot joint center of the patient.

With such a configuration, if the hip joint center, the knee joint center, and the foot joint center overlap with the metal bar in a plan view, it is determined that adjustment in alignment of the knee joint center is complete. On the other hand, if the three joint centers do not overlap with the metal bar in a plan view, the alignment adjustment is performed by adjusting the osteotomy angles at the distal part and the proximal part, and the like.

However, artificial knee joint replacement surgery is typically performed by making an incision only in the periphery of the knee joint of the patient. Accordingly, when performing the alignment measurement, the surgeon cannot view the hip joint center of the patient. Therefore, conventionally, the surgeon checks, with his or her eyes, the position that is thought to be the hip joint center of the patient, and arranges the metal bar at this position that is thought to be the hip joint center. Accordingly, there are often cases where the hip joint center of the patient and the position of the metal bar are misaligned in a plan view, and it is difficult to perform knee joint alignment measurement with accuracy.

In view of the above-described circumstances, it is an object of the present invention to provide a measuring instrument for use in artificial knee joint replacement surgery that can perform knee joint alignment measurement more accurately.

Means for Solving the Problem (1) In order to achieve the above-described object, according to the present invention, a measuring instrument for use in artificial knee joint replacement surgery, which is used in artificial knee joint replacement surgery, includes a guide section for indicating, from the outside of a patient, a position of a femoral head center of a hip joint of the patient, wherein the guide section is configured to indicate the position of the femoral head center while being arranged based on preliminarily measured relative positions of a reference area and the femoral head center of the patient, the reference area being viewable from the outside of the patient.

Note that "indicating a position of a femoral head center" in this context means both indicating the position itself of the femoral head center, and indicating, with a predetermined straight line, that the position of the femoral head center is located on the straight line.

According to this configuration, for example, the patient is subjected to X-ray photography prior to the artificial knee joint replacement surgery, and thereby the relative positions of the reference area and the femoral head center are measured with accuracy. Also, during the artificial knee joint replacement surgery, the reference area that can be viewed from the outside of the patient is used as a mark, and the information regarding the relative positions is used, so that the position of the femoral head center that cannot be viewed is detected with accuracy. Also, the guide section is installed so as to indicate the position of the detected femoral head center. Accordingly, the surgeon can correctly recognize the position of the femoral head center of the patient using the guide section when performing the artificial knee joint replacement surgery. Therefore, the surgeon can perform, more accurately, the adjustment in alignment in which the position of the knee joint center is adjusted using, for example, the femoral head center of the patient and the position of the foot joint center, which can be viewed from the outside of the patient, as a reference.

With this measure, according to the present invention, it is possible to provide the measuring instrument for use in artificial knee joint replacement surgery that can perform knee joint alignment measurement more accurately.

(2) Preferably, the guide section is arranged based on relative positions of a reference marker that is fixed to the reference area and the femoral head center.

According to this configuration, since the reference marker is fixed to the reference area, the surgeon can view the reference area more clearly. Therefore, for example, the surgeon can arrange the guide section so that the guide section indicates the position of the femoral head center more correctly.

(3) Preferably, the reference area includes an iliac spine of the patient.

According to this configuration, an iliac spine of the patient is a part that can easily be viewed by the surgeon from the outside of the patient. Accordingly, by setting the reference area at the iliac spine, it is possible for the surgeon to easily view the reference area at the time of the artificial knee joint replacement surgery.

(4) Preferably, the guide section includes a marker indicating section, and the marker indicating section indicates a femoral head center marker that extends, when viewed from the outside of the patient, in the longitudinal direction of the patient and passes through the femoral head center.

According to this configuration, the femoral head center marker can indicate the position of the femoral head center more clearly. Furthermore, for example, when this femoral head center marker is arranged so as to pass through the foot joint center of the patient, it is possible for the surgeon to perform the adjustment in alignment of the artificial knee joint using this marker as a reference in a plan view. In this case, for example, the surgeon can perform the adjustment in alignment so that the marker and the knee joint center overlap each other in a plan view.

(5) More preferably, the femoral head center marker is a laser beam, a metal bar, or a thread.

According to this configuration, when the marker is a laser beam, by adjusting the position, orientation, and the like of the laser light source, it is possible to easily adjust the position of the marker. Furthermore, it is possible to save the effort of carrying the marker. When the marker is a metal bar, with a simple configuration in which the metal bar is arranged so as to overlap the femoral head center in a plan view, it is possible for the marker to indicate the position of the femoral head center. When the marker is a thread, with a simple configuration in which the thread is extended near the body of the patient, it is possible for the marker to indicate the position of the femoral head center.

(6) Preferably, a fixation section for fixing the guide section to the patient is further included.

According to this configuration, the guide section can more reliably maintain the state of correctly indicating the position of the femoral head center.

(7) More preferably, the fixation section is configured to be fixed to an ankle of the patient, the guide section includes a first marker indicating section and a second marker indicating section, the first marker indicating section indicates a first marker that is shaped as a straight line that passes through the reference area of the patient, the second marker indicating section indicates a second marker that is shaped as a straight line, and the second marker is a femoral head center marker that extends, when viewed from the outside of the patient, in the longitudinal direction of the patient and passes through the femoral head center.

According to this configuration, the fixation section is arranged at a position at which it does not interfere with the artificial knee joint replacement surgery performed by the surgeon. Accordingly, the surgeon can more smoothly perform the artificial knee joint replacement surgery. Furthermore, by providing the first marker indicating the reference area of the patient and the second marker indicating the femoral head center separately, it is possible to adjust the positions of the markers independently. As a result, the position of the femoral head center can be more correctly indicated to the surgeon with the markers.

(8) More preferably, the first marker and the second marker are configured to be arranged parallel to each other, and a distance between the first marker and the second marker in a left/right direction of the patient corresponds to a distance between the reference area and the femoral head center in the left/right direction.

According to this configuration, the measuring device can indicate the position of the femoral head center using the markers more correctly.

(9) Preferably, the fixation section is configured to be fixed to the pelvis of the patient, the guide section includes a marker indicating section, and the marker indicating section is arranged at the femoral head center based on preliminarily measured relative positional relationship between the reference area and the femoral head center.

According to this configuration, the marker indicating section is arranged at the femoral head center. Accordingly, the marker indicating section itself functions as a mark indicating the femoral head center. The surgeon can thus view the position of the femoral head center more clearly.

Effects of the Invention

According to the present invention, it is possible to provide a measuring instrument for use in artificial knee joint replacement surgery that can perform knee joint alignment measurement more accurately.

BRIEF DESCRIPTION OF THE DRAWINGS

FIG. 12 is a plan view illustrating a measuring instrument and the like.

DESCRIPTION OF EMBODIMENTS

Hereinafter, embodiments for implementing the present invention will be described with reference to the drawings. Note that the present invention is widely applicable as a measuring instrument for use in artificial knee joint replacement surgery, which is used for artificial knee joint replacement surgery.

Figure 1:
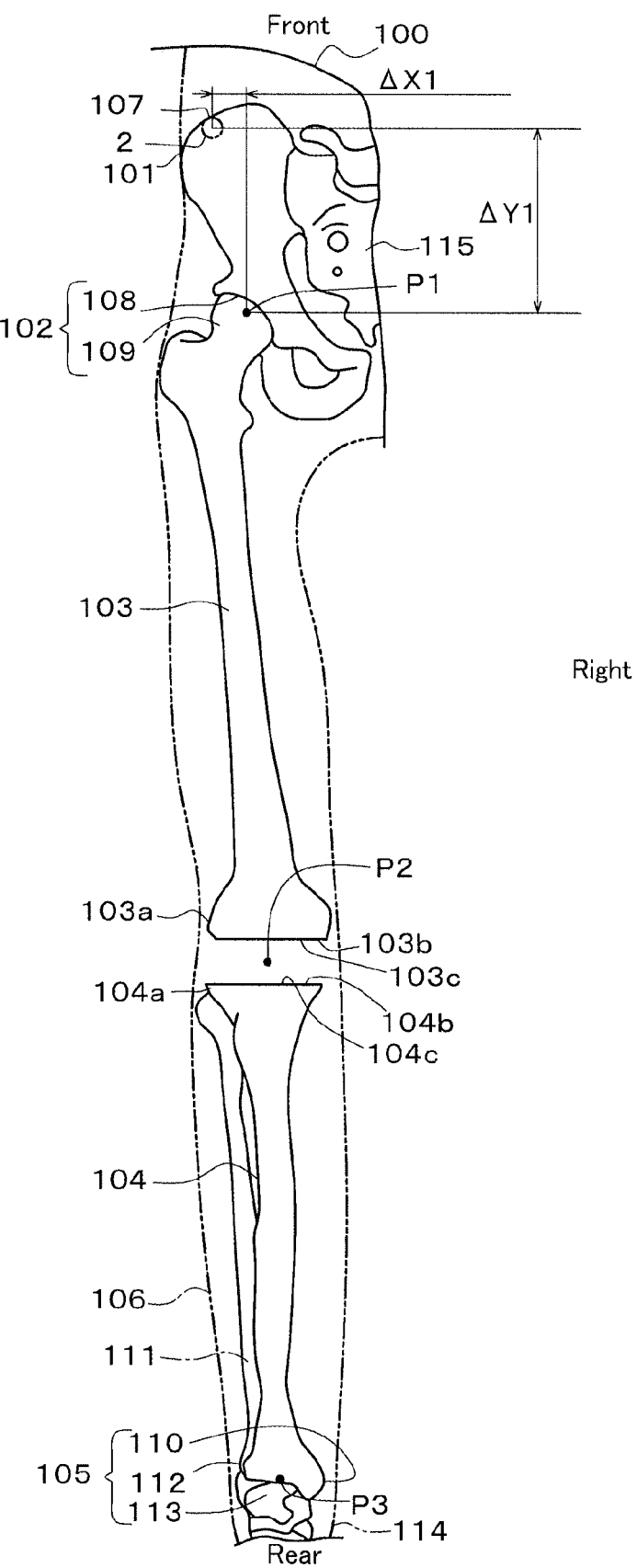
FIG. 1 is a plan view schematically illustrating a part of a patient that is relevant to artificial knee joint replacement surgery.

Note that the schematic configuration of the body of a patient who is to undergo artificial knee joint replacement surgery will be described prior to the description of the measuring instrument for use in artificial knee joint replacement surgery. FIG. 1 is a plan view schematically illustrating a part of a patient 100 that is relevant to artificial knee joint replacement surgery. In FIG. 1, the patient 100 is shown in a state of being laid on a surgical table (not shown). Furthermore, in FIG. 1, parts of the patient 100 other than the bones are shown with two-dot chain lines, which are imaginary lines.

Note that, in the present embodiment, upper/lower, front/rear, and left/right refer to the upper/lower, front/rear, and left/right for a surgeon in the standing position. That is, the upper/lower direction refers to the vertical direction, and the front/rear direction refers to the height direction of the patient 100 (in the direction in which the spine extends). Furthermore, the present embodiment is described taking the example of a case where the artificial knee joint replacement surgery is performed on the right knee of the patient 100.

The patient 100 has an iliac crest 101, a hip joint 102, a femur 103, a tibia 104, a foot joint 105, and a skin 106. Note that FIG. 1 shows the state in which the artificial knee joint replacement surgery is underway on the patient 100, and a distal part 103a of the femur 103 and a proximal part 104a of the tibia 104 of the patient 100 have been subjected to osteotomy.

The iliac crest 101 has an anterior superior iliac spine 107. The anterior superior iliac spine 107 is an example of a "reference area" of the present invention. The anterior superior iliac spine 107 is a part of the patient 100 that can be viewed from the outside of the patient 100, and is exposed to the surface of the patient 100 through the skin 106 of the patient 100. Note that, during the artificial knee joint replacement surgery, a surgical cover cloth (not shown) is overlaid on the lower half of the patient 100, but the anterior superior iliac spine 107 can be viewed through this surgical cover cloth by the surgeon.

The hip joint 102 has an acetabuli 108 and a femoral head 109. The acetabuli 108 has a recess-like part. This recess-like part receives the femoral head 109. The femoral head 109 is a hemispherical part that is formed in the proximal part of the femur 103. Part of the femoral head 109 is inserted into the recess-like part of the acetabuli 108. A femoral head center P1, which serves as the center of rotation of the femoral head 109, is defined as the center of the hip joint 102. The femoral head 109 slides relative to the acetabuli 108 around the femoral head center P1.

The foot joint 105 has an inner malleolus 110, which is formed in the distal part of the tibia 104, an outer malleolus 112, which is formed in the distal part of a calf bone 111, and an anklebone 113. A foot joint center P3 is defined at a substantially central position between the inner malleolus 110 and the outer malleolus 112. The anklebone 113 slides relative to the inner malleolus 110 and the outer malleolus 112 around the foot joint center P3.

In the artificial knee joint replacement surgery, the distal part 103a of the femur 103 and the proximal part 104a of the tibia 104 of the patient 100 are subjected to osteotomy. Then, an artificial knee joint component (not shown in FIG. 1) is installed on the distal part 103a and the proximal part 104a.

Figure 2:
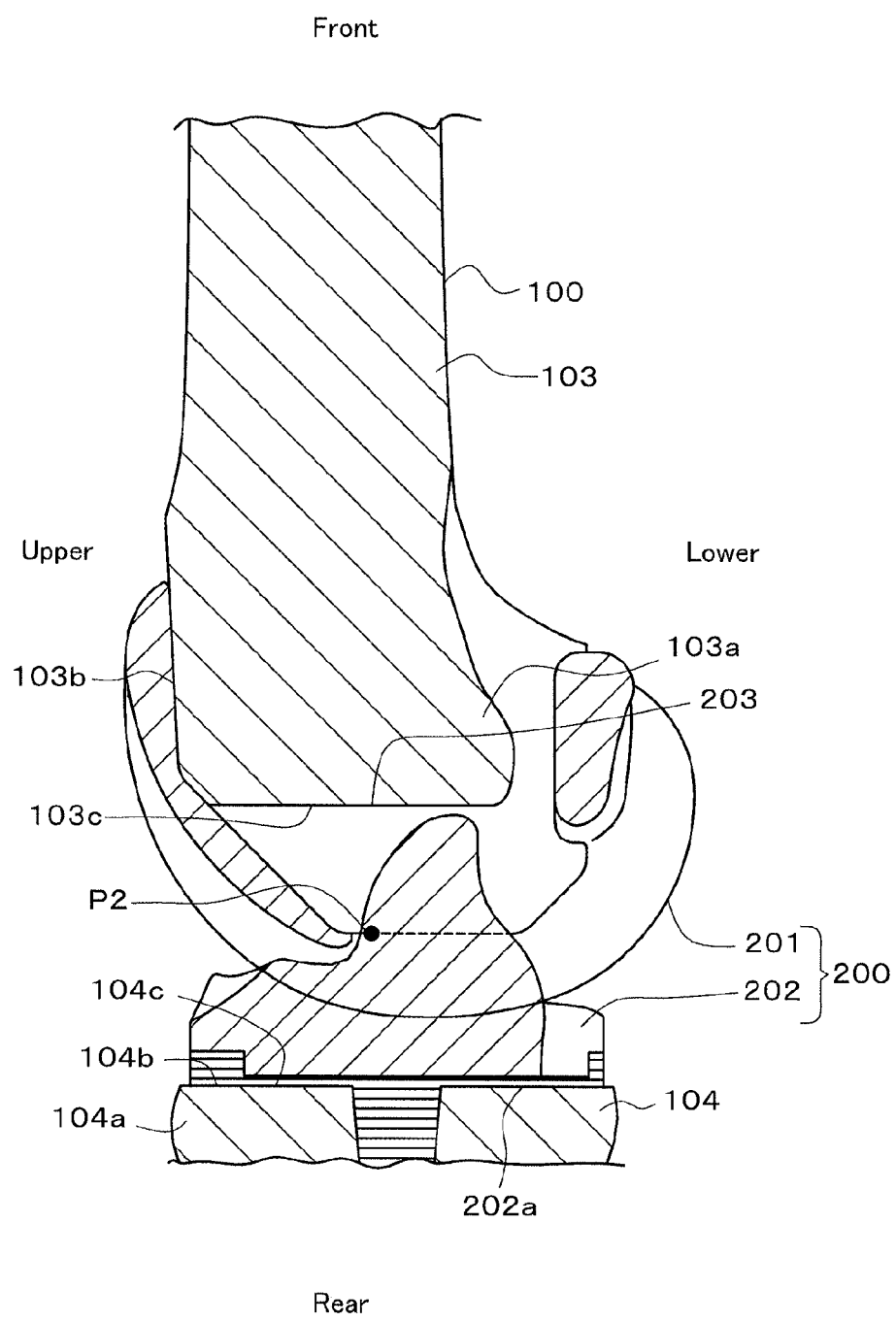
FIG. 2 is a partial cross-sectional view illustrating an artificial knee joint component, a femur of the patient, and a tibia of the patient, in a state viewed from lateral of the patient.

FIG. 2 is a partial cross-sectional view illustrating an artificial knee joint component 200, and the femur 103 and the tibia 104 of the patient, in the state viewed from lateral of the patient. Note that in FIG. 2, the femur 103 and the like are shown in cross-section.

Referring to FIG. 2, the artificial knee joint component 200 is used in order to recover the knee function of the patient who has a knee joint that is highly-deformed due to, for example, knee osteoarthritis, chronic articular rheumatism, or the like to the regular function.

The artificial knee joint component 200 has a femoral component 201 and a tibial component 202.

The femoral component 201 is fixed to the distal part 103a of the femur 103. Furthermore, the tibial component 202 is fixed to the proximal part 104a of the tibia 104. The femoral component 201 and the tibial component 202 slide relative to each other in accordance with knee bending and extending movement of the patient. Accordingly, the cooperation of the femoral component 201 and the tibial component 202 guides a bending operation of the femur 103 relative to the tibia 104.

Note that, in the following, "inner" and "outer" refer to the inner side and outer side of the knee of the patient in which the artificial knee joint component 200 is installed.

That is, if the artificial knee joint component 200 is arranged on the right leg of the patient, "inner" refers to the left side of the patient, and "outer" refers to the right side of the patient.

The femoral component 201 is U-shaped in a side view. The inner surface of the femoral component 201 that faces the distal part 103a of the femur 103 provides a fixing surface 203. The fixing surface 203 is provided in order to fix the femoral component 201 to an osteotomy surface 103b of the femur 103.

The osteotomy surface 103b is a surface that is artificially formed in the artificial knee joint replacement surgery by the surgeon. The osteotomy surface 103b is formed by, for example, the surgeon cuffing off a part of the distal part 103a using an instrument such as a cutter. The osteotomy surface 103b has, for example, a downward-facing surface 103c, which is a surface that faces downward. The downward-facing surface 103c is a flat surface.

The orientation of the femoral component 201 relative to the femur 103 depends on the orientation of the downward-facing surface 103c. The femoral component 201 having the above-described configuration is slidably supported by the tibial component 202.

The tibial component 202 is fixed to an osteotomy surface 104b, which is formed in the proximal part 104a of the tibia 104. The osteotomy surface 104b is a surface that is artificially formed in the artificial knee joint replacement surgery by the surgeon. The osteotomy surface 104b is formed by, for example, the surgeon cutting off a part of the proximal part 104a using an instrument such as a cutter. The osteotomy surface 104b has, for example, an upward-facing surface 104c, which is a surface that faces upward. The upward-facing surface 104c is a flat surface. The upward-facing surface 104c is in surface contact with a lower surface 202a of the tibial component 202, and receives the lower surface 202a.

The orientation of the tibial component 202 relative to the tibia 104 depends on the orientation of the upward-facing surface 104c. The upper part of the tibial component 202 can slide relative to the femoral component 201 while being in contact with the femoral component 201. With the above-described configuration, when the patient 100 bends and extends the knee, the femoral component 201 and the tibial component 202 swing about a knee joint center P2, and as a result, bending and extending movement of the knee of the patient 100 is realized.

Referring to FIG. 1, prior to installation of the above-described artificial knee joint component 200, the patient 100 is subjected to the measurement of the relative positional relationship between the position of the femoral head center P1 of the hip joint 102 and the position of the anterior superior iliac spine 107 (central position of the anterior superior iliac spine 107) of the patient 100 using a noncontact measurement device such as an X-ray measurement device. For example, an examination using the X-ray measurement device is conducted on the patient 100 to measure the relative positional relationship between the femoral head center P1 and the anterior superior iliac spine 107. With this examination, respective relative distances $\Delta X1$ and $\Delta Y1$ between the anterior superior iliac spine 107 and the femoral head center P1 in the left/right and upper/lower directions are measured. Note that the anterior superior iliac spine 107 is an example of the "reference area" of the present invention, and refers to an area of the patient 100 that the surgeon can view from the outside of the patient 100.

Note that, for example, a device other than the X-ray measurement device, such as a CT scan device, may be used to measure the relative positions of the femoral head center P1 and the anterior superior iliac spine 107 of the patient 100. After the measurement of the relative positions, the patient 100 undergoes the artificial knee joint replacement surgery. At the time of the artificial knee joint replacement surgery, the surgeon performs adjustment in alignment of the knee joint of the patient 100 using a measuring instrument 1 for use in artificial knee joint replacement surgery (hereinafter, also referred to simply as "measuring instrument 1").

Figure 3:
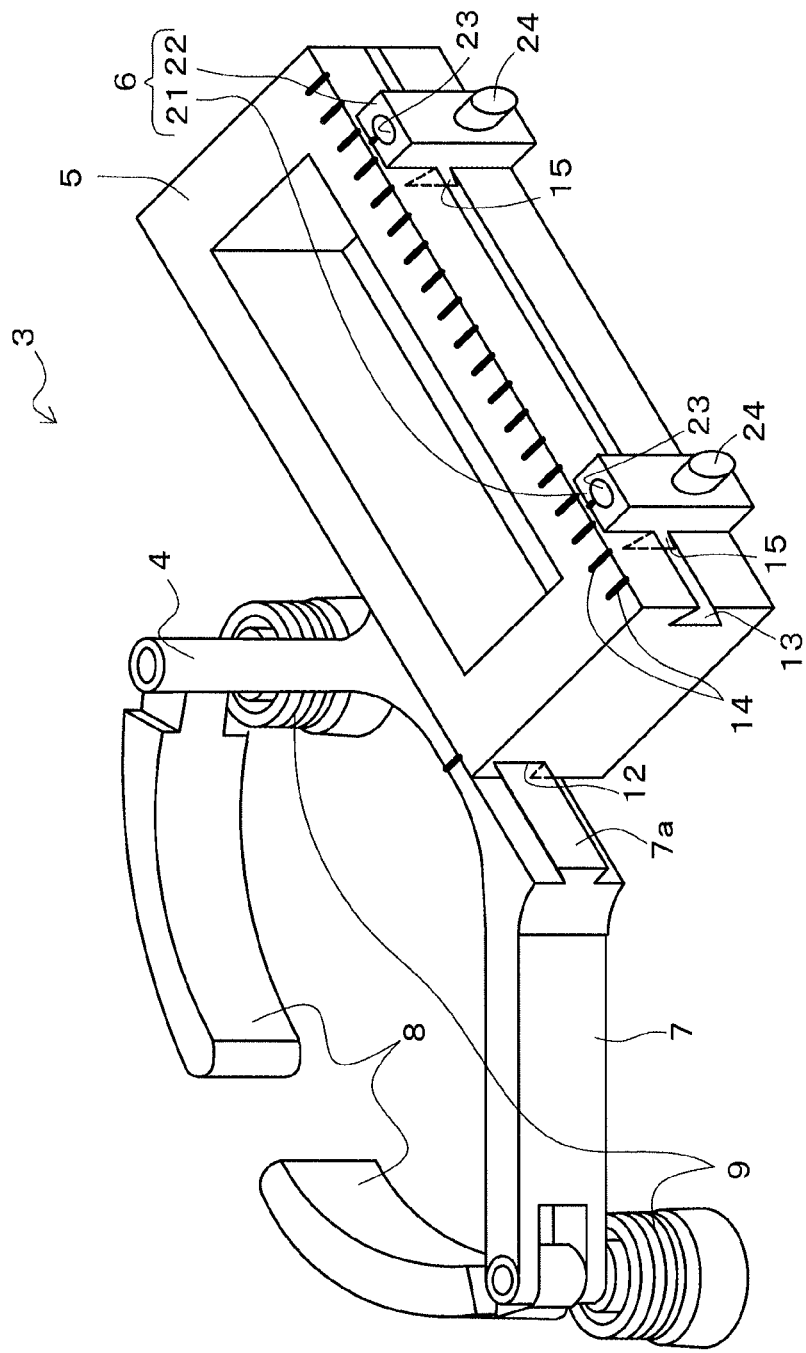
FIG. 3 is a perspective view illustrating a measuring instrument.
Figure 4:
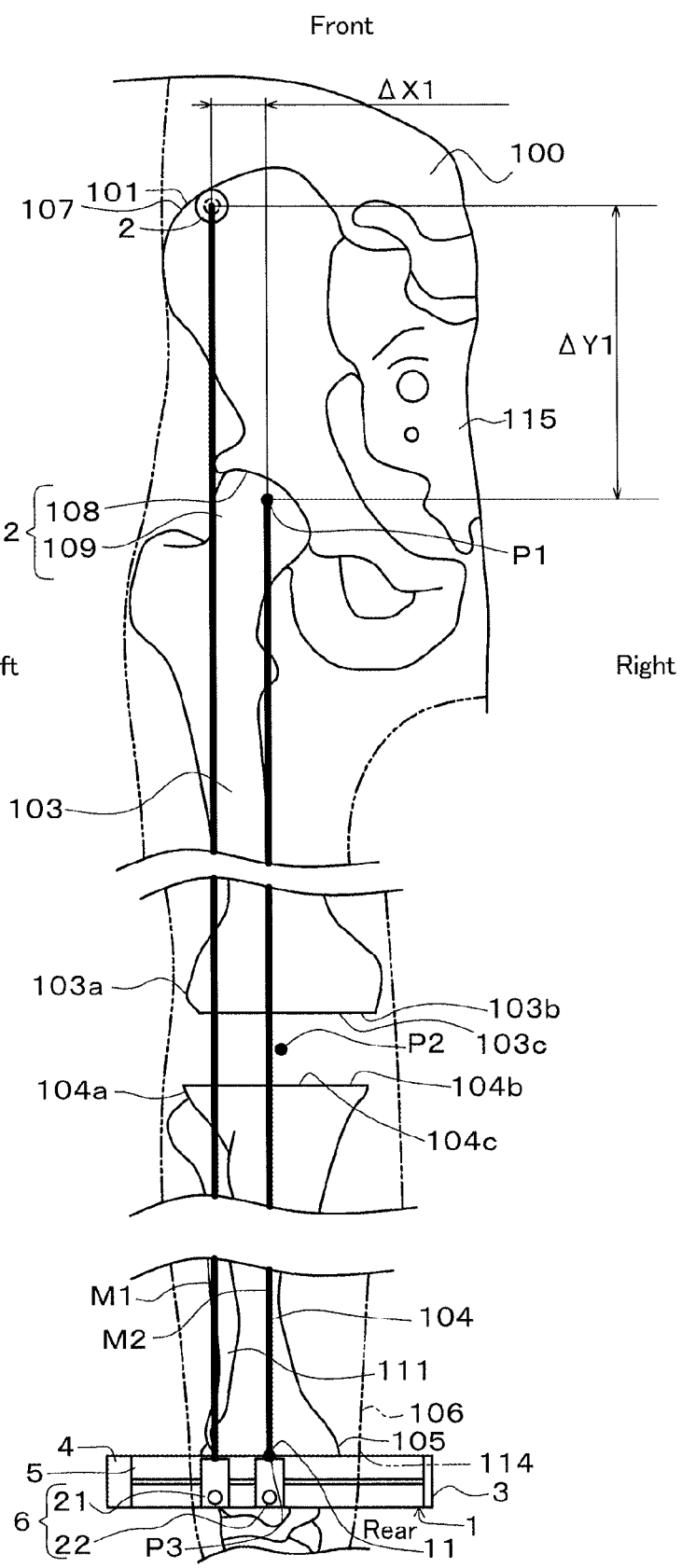
FIG. 4 is a schematic plan view illustrating the state in which the measuring instrument is fixed to the patient.

FIG. 3 is a perspective view of the measuring instrument 1. FIG. 4 is a plan view schematically illustrating the state in which the measuring instrument 1 is fixed to the patient 100. Referring to FIGS. 3 and 4, the measuring instrument 1 is an instrument for use in adjustment in alignment of the knee joint of the patient 100. In the present embodiment, "adjustment in alignment" refers to a procedure that is performed so that the femoral head center P1 of the hip joint 102, the knee joint center P2, and the foot joint center P3 of the foot joint 105 of the patient 100 are lined up in a straight line in a plan view from the outside of the patient 100.

In the present embodiment, the measuring instrument 1 is fixed to an ankle 114 or the like of the patient 100, and performs display necessary for the adjustment in alignment of the patient 100 using a laser beam.

The measuring instrument 1 includes a reference marker 2 and a guide unit 3. Note that the reference marker 2 may be provided as a member separate from the measuring instrument 1.

The reference marker 2 is provided as a member that is fixed to the anterior superior iliac spine 107. The reference marker 2 has a shape that has, for example, an elongated bar-like pin section made of metal, and a colored head section. The head section is colored in white, for example. The pin section of the reference marker 2 is fixed to the patient 100 by being screwed into a hole formed in the anterior superior iliac spine 107 with a drill or the like. The reference marker 2 protrudes upward from the patient 100. Note that the reference marker 2 is not limited to the above-described shape. The reference marker 2 may have any configuration as long as it indicates the anterior superior iliac spine 107, and may be, for example, a mark provided on the patient 100 in a color such as black.

In the present embodiment, the guide unit 3 is fixed to the ankle 114 of the patient 100. This guide unit 3 is configured to indicate the anterior superior iliac spine 107, and indicate the position of the femoral head center P1.

The guide unit 3 includes a fixation section 4, a movable base 5, and a guide section 6.

The fixation section 4 is an ankle clamp that is fixed to the ankle 114 of the patient 100. The fixation section 4 is provided in order to fix the movable base 5 and the guide section 6 to the ankle 114 of the patient 100.

The fixation section 4 has a fixed arm 7 and a pair of movable arms 8.

The fixed arm 7 is a V-shaped member. The fixed arm 7 is arranged on, for example, the upper side of the ankle 114. The pair of front ends of the fixed arm 7 is connected to the pair of movable arms 8 via hinge sections. The pair of movable arms 8 is swingable relative to the fixed arm 7, and cooperates with the fixed arm 7 so as to sandwich the ankle 114 in the state in which the fixed arm 7 is placed on the upper side of the ankle 114. Torsional springs 9 are attached to respective connections between the pair of movable arms 8 and the fixed arm 7.

Each torsional spring 9 biases the front end of the corresponding movable arm 8 in the direction in which the front end of the corresponding movable arm 8 approaches the fixed arm 7. In order to fix the fixation section 4 to the ankle 114, the surgeon displaces the front ends of the pair of movable arms 8 in the direction of separation from the fixed arm 7 to increase the distance between the front ends of the pair of movable arms 8. The surgeon places the fixed arm 7 in this state on the ankle 114, and then releases the pair of movable arms 8. Accordingly, the spring force of the torsional springs 9 displaces the front ends of the pair of movable arms 8 toward the fixed arm 7. As a result, the ankle 114 is sandwiched between the pair of movable arms 8 and the fixed arm 7.

A first indicator 11 is formed on one side surface of the intermediate section of the fixed arm 7 that faces the hip joint 102 of the patient 100. The first indicator 11 indicates the central position, in the left/right direction, of the fixation section 4. The guide unit 3 is arranged so that the first indicator 11 and the foot joint center P3 match each other in a plan view.

A fixed rail 7a is formed on the upper surface of the intermediate section of the fixed arm 7. The fixed rail 7a is formed with a straight line shape, and extends in the left/right direction in the state in which the fixation section 4 is fixed to the ankle 114. Note that the state in which the fixation section 4 is fixed to the ankle 114 is hereinafter also referred to simply as "fixed state of the fixation section 4". The fixed rail 7a has a trapezoidal cross-section that is orthogonal to the longitudinal direction of the fixed rail 7a. In other words, in the fixed state of the fixation section 4, the fixed rail 7a has an inverse tapered shape such that width of the fixed rail 7a in the front/rear direction increases toward the upper side. The movable base 5 is connected to the fixed rail 7a.

The movable base 5 is provided as a section that supports the guide section 6, and is displaceable relative to the fixation section 4 in the left/right direction. The movable base 5 is a rectangular ring member, and is made of a metal plate member and the like. The movable base 5 extends in an elongated manner in the left/right direction in the present embodiment.

The movable base 5 has a lower rail 12 and an upper rail 13.

The lower rail 12 is slidably connected to the fixed rail 7a. The lower rail 12 is a recess-like part formed on the lower surface of the movable base 5, and extends in the left/right direction. The lower rail 12 has a shape that corresponds to the shape of the fixed rail 7a. In the present embodiment, the lower rail 12 has an inverse tapered shape such that width of the lower rail 12 in the front/rear direction decreases toward the lower side. According to this configuration, the lower rail 12 in the state of being engaged with the fixed rail 7a is restricted from being disengaged upward from the fixed rail 7a. The movable base 5 is slidable relative to the fixation section 4 in the left/right direction. The upper rail 13 is formed at the upper end of the movable base 5.

The upper rail 13 is provided in order to hold the guide section 6. The upper rail 13 is a recess-like part formed on the upper surface of the movable base 5, and extends in the left/right direction. The upper rail 13 has an inverse tapered shape such that width of the upper rail 13 in the front/rear direction decreases toward the upper side. The upper rail 13 is arranged adjacent to a second indicator 14.

The second indicator 14 is formed on one side surface of the movable base 5 that faces the hip joint 102 of the patient 100. The second indicator 14 has a plurality of scale marks that are equally spaced in the left/right direction. The surgeon adjusts the position of the guide section 6 in the left/right direction while referencing the first indicator 11 and the second indicator 14.

The guide section 6 is provided in order to indicate the position of the femoral head center P1 of the hip joint 102 of the patient 100 from the outside of the patient 100. The guide section 6 is configured to indicate the position of the femoral head center P1 while being arranged based on the preliminarily measured relative positions of the anterior superior iliac spine 107 and the femoral head center P1. In the present embodiment, the reference marker 2 is provided on the anterior superior iliac spine 107, and the guide section 6 is arranged based on the relative positions of the center of the reference marker 2 and the femoral head center P1. The guide section 6 is arranged on the upper part of the movable base 5.

The guide section 6 has a first marker indicating section 21 and a second marker indicating section 22.

In the present embodiment, the marker indicating sections 21 and 22 have laser light sources, have the same configuration, and are arranged to emit a laser beam such as a red laser beam. In the present embodiment, the laser beam from the first marker indicating section 21 is defined as a first marker M1. Furthermore, the laser beam of the second marker indicating section 22 is defined as a second marker M2. Each of the marker indicating sections 21 and 22 has a light emitting surface 23 that faces the head part (frontward) of the patient 100, and emits a laser beam frontward from the light emitting surface 23. The laser beams are linear in a plan view as shown in FIG. 4, and are emitted onto the patient 100 from the laser light sources in the shape of a fan in a side view. Accordingly, the surgeon can view the position of the laser beam emitted onto the body surface of the patient.

The marker indicating sections 21 and 22 each have a lower rail 15. The lower rails 15 are parts that are connected to the upper rail 13 of the movable base 5, and are configured to slide the marker indicating sections 21 and 22 relative to the movable base 5 in the left/right direction. The lower rails 15 are protrusion-like parts respectively formed on the lower surfaces of the marker indicating sections 21 and 22, and extend in the left/right direction.

Each lower rail 15 has a shape that corresponds to the shape of the upper rail 13. In the present embodiment, the lower rail 15 has an inverse tapered shape such that width of the lower rail 15 in the front/rear direction decreases toward the upper side. According to this configuration, the lower rail 15 in the state of being engaged with the upper rail 13 is restricted from being disengaged upward from the upper rail 13.

The marker indicating sections 21 and 22 are respectively provided with fixing screws 24. The fixing screws 24 pass through the corresponding marker indicating sections 21 and 22 in the upper/lower direction of marker indicating sections 21 and 22. The fixing screws 24 are screwed into female threaded sections (not shown) formed in the respective marker indicating sections 21 and 22. When the fixing screw 24 is screwed into the corresponding female threaded section by a predetermined amount or more, the front end of the fixing screw 24 presses the upper surface of the movable base 5. Accordingly, the upper rail 13 and the lower rail 15 are pulled by each other, and friction resistance occurs. Accordingly, the marker indicating sections 21 and 22 are fixed to the movable base 5.

The first marker indicating section 21 is provided in order to indicate the linear first marker M1 that passes through the anterior superior iliac spine 107 (reference marker 2) of the patient 100. The first marker indicating section 21 displays the first marker M1 that extends in the front/rear direction, which is a direction orthogonal to the longitudinal direction of the movable base 5 (left/right direction).

The second marker indicating section 22 is provided in order to indicate the linear second marker M2 that passes through the position of the femoral head center P1 of the patient 100. The first marker indicating section 21 and the second marker indicating section 22 are side-by-side in the left/right direction while positions of the first marker indicating section 21 and the second marker indicating section 22 in the front/rear direction are aligned with each other.

The second marker M2 that is emitted from the second marker indicating section 22 is an example of a "femoral head center marker" of the present invention. The second marker M2 is emitted from the second marker indicating section 22 so as to extend in the longitudinal direction of the patient 100 (front/rear direction) and pass through the femoral head center P1 in a plan view from the outside of the patient 100.

In the present embodiment, the first marker M1 and the second marker M2 are arranged parallel to each other. That is, the light emitting surfaces 23 of the marker indicating sections 21 and 22 are oriented in the same direction. As will be described later, the distance, in the left/right direction, between the first marker M1 and the second marker M2 is set to the same value as the distance ΔX1, in the left/right direction, between the center of the reference marker 2 and the femoral head center P1.

The second marker indicating section 22 is arranged on the inner side of the patient 100 in the left/right direction relative to the first marker indicating section 21. Accordingly, the second marker M2 is emitted so as to pass through the foot joint center P3 in a plan view.

Figure 5:
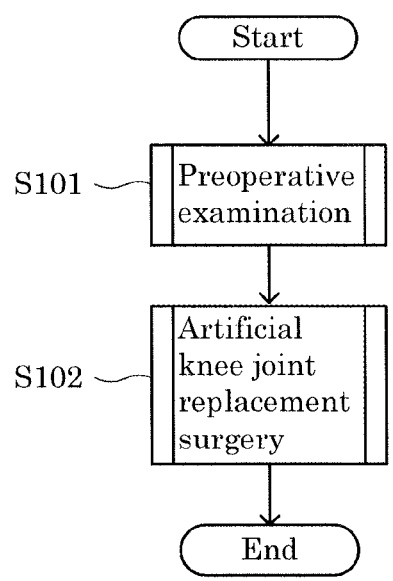
FIG. 5 is a flowchart illustrating an example of a flow of a procedure regarding the artificial knee joint replacement surgery.

The above is the schematic configuration of the measuring instrument 1. The following will describe the outline of a flow of treatment regarding the artificial knee joint replacement surgery. FIG. 5 is a flowchart illustrating an example of the flow of treatment regarding the artificial knee joint replacement surgery. Note that the description of the flowchart will be given suitably by referencing figures other than this flowchart as well as necessary.

Referring to FIG. 5, when artificial knee joint replacement surgery is to be performed, a preoperative examination is performed first (step S101). Then, the artificial knee joint replacement surgery is performed (step S102). The following will describe the preoperative examination in more detail.

Figure 6:
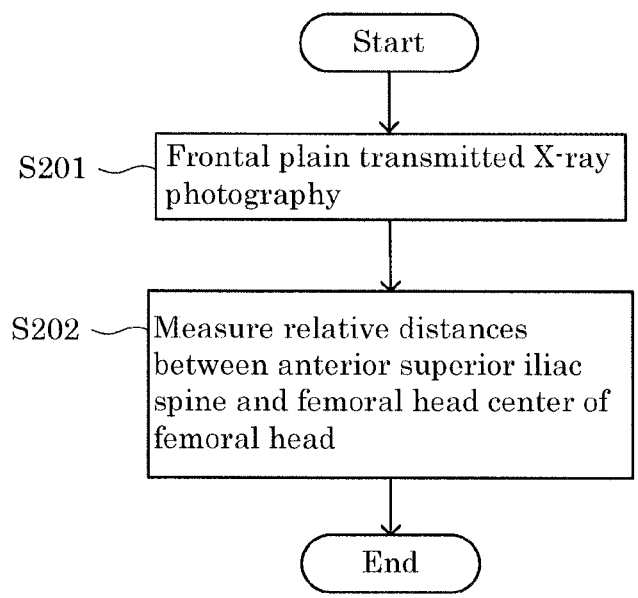
FIG. 6 is a flowchart illustrating an example of a flow of a preoperative examination (step S101).

FIG. 6 is a flowchart illustrating an example of a flow of the preoperative examination (step S101). Referring to FIG. 6, in the preoperative examination, the patient 100 is first subjected to frontal plain transmitted X-ray photography (step S201). Accordingly, an X-ray picture (transmission image) of the anterior superior iliac spine 107, the hip joint 102, the femur 103, the tibia 104, and the foot joint 105 of the patient 100 is obtained.

Figure 7:
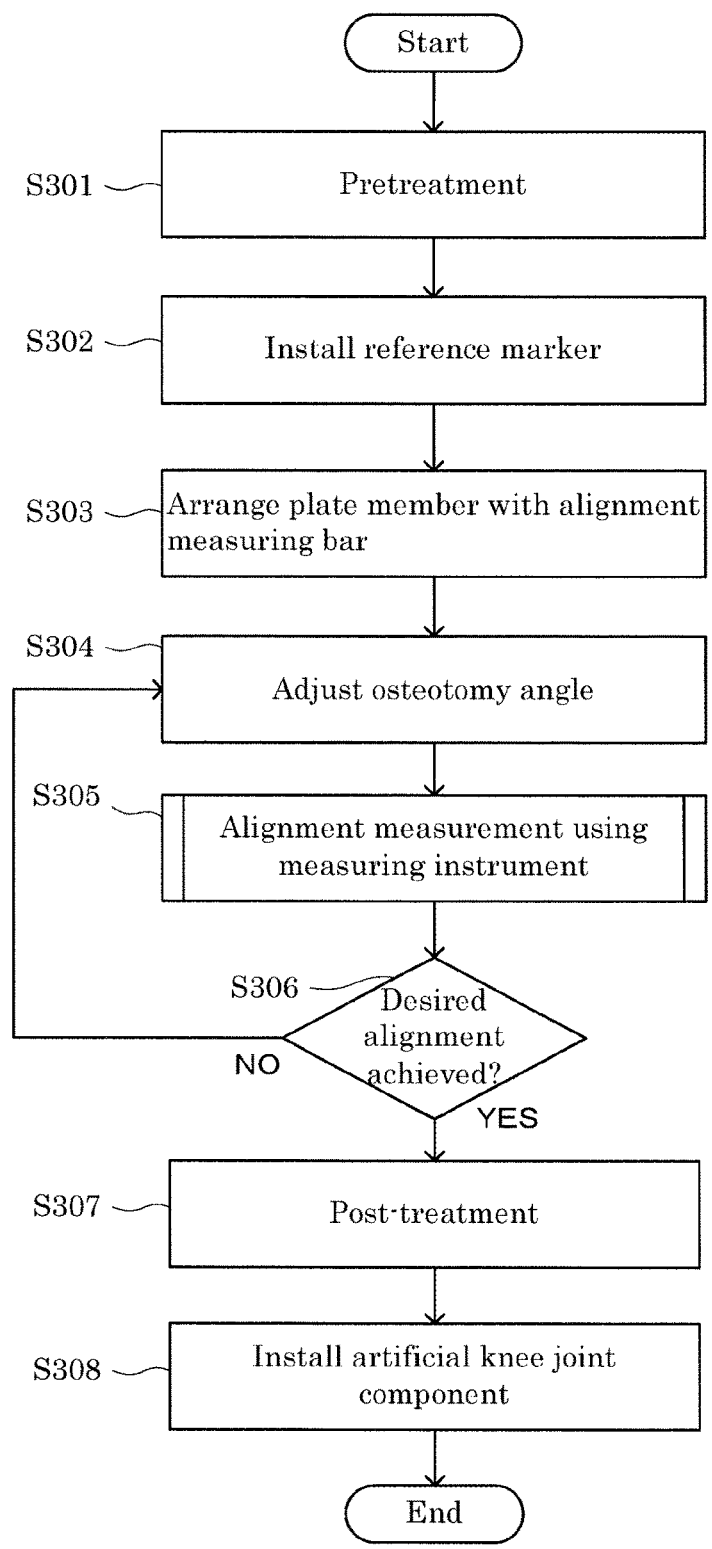
FIG. 7 is a flowchart illustrating an example of a flow of the artificial knee joint replacement surgery (step S102).

Then, based on the X-ray picture, the surgeon measures the relative distances ΔX1 and ΔY1 between the anterior superior iliac spine 107 and the femoral head center P1 of the femoral head 109 (step S202). The above is an example of the flow of the preoperative examination. The following will describe the artificial knee joint replacement surgery FIG. 7 is a flowchart illustrating an example of a flow of the artificial knee joint replacement surgery (step S102). Referring to FIG. 7, in the artificial knee joint replacement surgery, pretreatment is performed (step S301). In the present embodiment, "pretreatment" refers to a procedure for achieving the state in which the artificial knee joint component 200 can be inserted between the distal part 103a of the femur 103 and the proximal part 104a of the tibia 104.

Specifically, the pretreatment includes treatment for making an incision in the skin in the vicinity of the knee joint of the patient 100, treatment for cutting off the ligament that is no longer needed after the artificial knee joint component 200 is installed, an osteotomy treatment that is performed on the distal part 103a of the femur 103, and an osteotomy treatment that is performed on the proximal part 104a of the tibia 104. The osteotomy treatment that is performed on the distal part 103a of the femur 103 forms the flat downward-facing surface 103c in the distal part 103a. The osteotomy treatment that is performed on the proximal part 104a of the tibia 104 forms the flat upward-facing surface 104c in the proximal part 104a.

After the pretreatment, the reference marker 2 is installed (step S302). At this time, the surgeon forms a hole in the anterior superior iliac spine 107 of the patient 100 using a drill or the like, and embeds a part of the reference marker 2 into this hole. Accordingly, the reference marker 2 is in the state of protruding upward from the anterior superior iliac spine 107.

Figure 8:
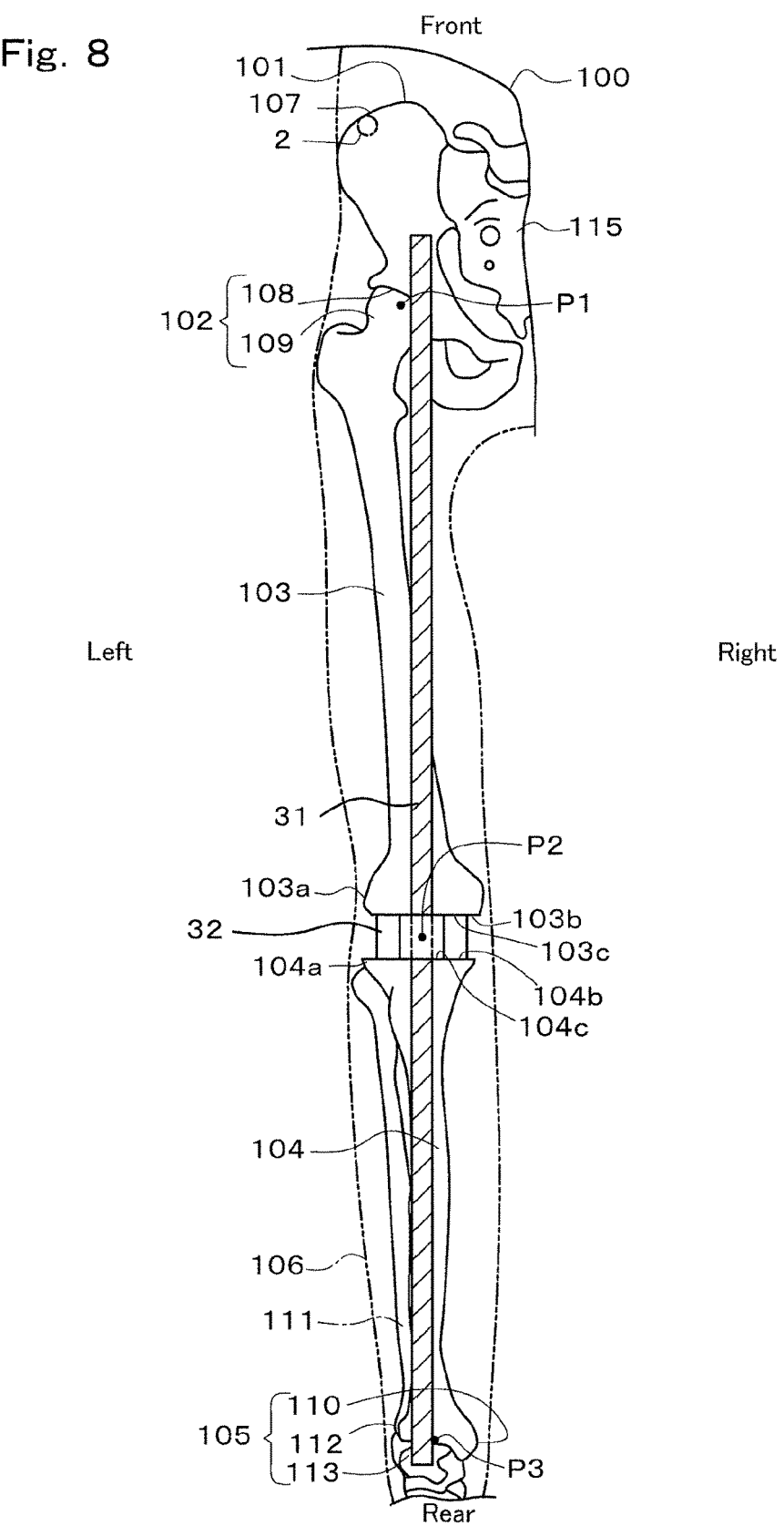
FIG. 8 is a schematic diagram illustrating the state in which a plate member with an alignment measuring bar attached thereto is arranged on the patient.

Then, as shown in FIG. 8, a plate member 32 with an alignment measuring bar 31 attached to the plate member 32 is arranged (step S303). FIG. 8 is a schematic diagram illustrating the state in which the plate member 32 with the alignment measuring bar 31 attached to the plate member 32 is arranged on the patient 100. Note that a part of the alignment measuring bar 31 is hatched in the figure. The plate member 32 has the shape of a flat plate having a predetermined thickness, and is arranged so as to be sandwiched between the downward-facing surface 103c of the distal part 103a and the upward-facing surface 104c of the proximal part 104a. A part that projects from the plate member 32 has a through-hole extending in the front/rear direction, and the alignment measuring bar 31 is inserted through the through-hole.

Accordingly, the alignment measuring bar 31 is arranged so as to pass through, in a plan view, the knee joint center P2 between the distal part 103a and the proximal part 104a, for example. The alignment measuring bar 31 is arranged so as to pass through, in a plan view, the foot joint center P3 of the foot joint 105. At this time, the surgeon checks whether or not the alignment measuring bar 31 passes through the femoral head center P1 in a plan view.

Note that, if the relative distance, in the left/right direction, between the reference marker 2 and the position of the femoral head center P1 is not equal to the relative distance, in the left/right direction, between the reference marker 2 and the alignment measuring bar 31, the alignment measuring bar 31 is shifted from the position of the femoral head center P1 in a plan view.

Then, the surgeon adjusts the osteotomy angles based on a result of the measurement of the relative distance, in the left/right direction, between the reference marker 2 and the alignment measuring bar 31 (step S304). Specifically, the surgeon adjusts the orientations of the downward-facing surface 103c of the distal part 103a, the upward-facing surface 104c of the proximal part 104a, and the like.

Then, the surgeon performs alignment measurement using the measuring instrument 1 (step S305). In other words, it is measured whether or not the femoral head center P1 of the hip joint 102, the knee joint center P2, and the foot joint center P3 of the foot joint 105 are lined up on a straight line in a plan view. The alignment measurement will be described in detail later.

As a result of the alignment measurement, if the femoral head center P1, the knee joint center P2, and the foot joint center P3 are not lined up on a straight line in a plan view, it is determined that desired alignment has not been achieved (No, in step S306), and the treatment of step S304 is performed again. In this case, the surgeon adjusts the osteotomy angles so that the femoral head center P1, the knee joint center P2, and the foot joint center P3 are lined up on a straight line in a plan view (step S304).

On the other hand, as a result of the alignment measurement, if the femoral head center P1, the knee joint center P2, and the foot joint center P3 are lined up on a straight line in a plan view, it is determined that desired alignment has been achieved (Yes, in step S306), and the following treatment is performed. Specifically, post-treatment is performed (step S307). The post-treatment includes, for example, bone cut-off treatment, soft tissue adjusting treatment, trial installation treatment, and test reduce treatment.

The bone cut-off treatment is osteotomy treatment that is other than the osteotomy treatment of steps S301 and S304 and is needed for installation of the artificial knee joint component 200. The soft tissue adjusting treatment is treatment for performing positional adjustment and the like on a soft tissue of the patient 100 such as a collateral ligament. The trial installation treatment refers to treatment for installing a trial component having the same shape as that of the artificial knee joint component 200 on the distal part 103a and the proximal part 104a. The test reduce treatment is treatment for temporarily reducing the joint or the like that was dislocated at the time of the artificial knee joint replacement surgery to the original state.

Then, the surgeon performs treatment for installing the artificial knee joint component 200 in the patient 100 (step S308). Specifically, a predetermined joint or the like is again dislocated, and furthermore the trial component is removed from the patient 100. Then, the femoral component 201 of the artificial knee joint component 200 is fixed to the distal part 103a. Furthermore, the tibial component 202 is fixed to the proximal part 104a. Then, actual resetting for joining the dislocated joint or the like is performed.

Figure 9:
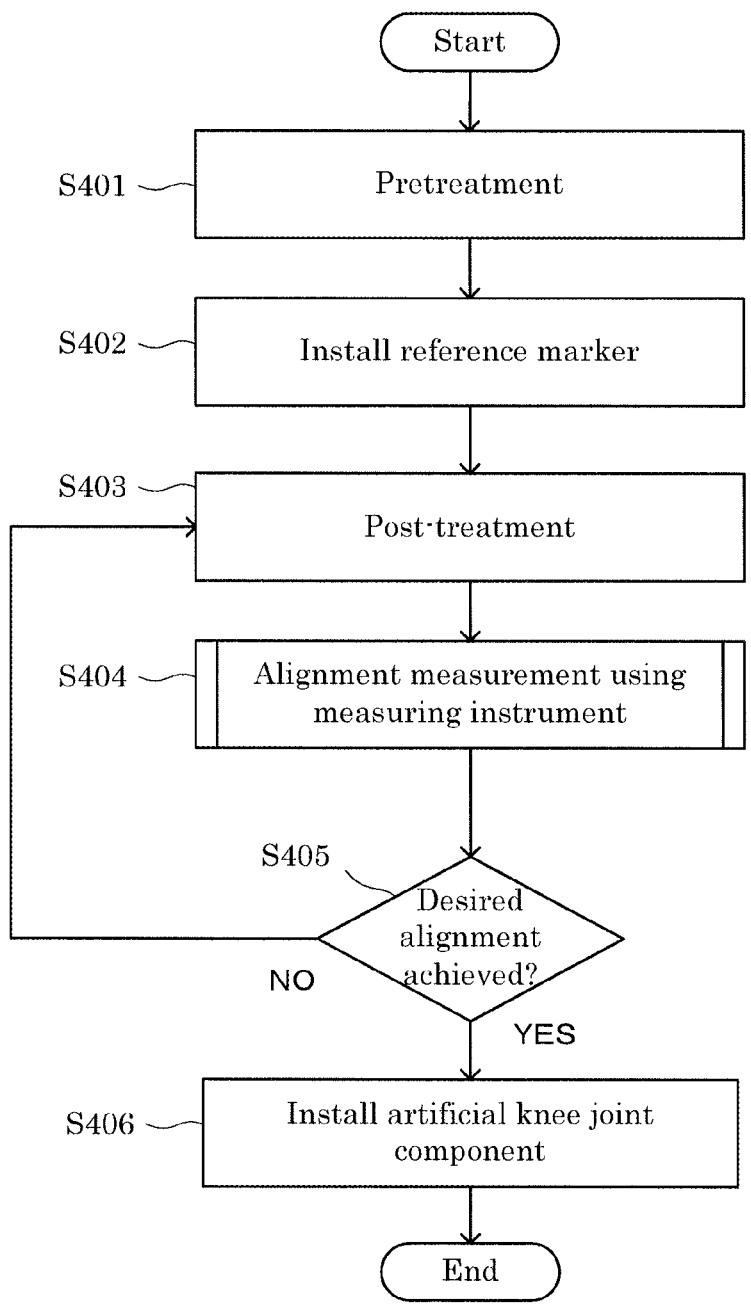
FIG. 9 is a flowchart illustrating another example of the flow of the artificial knee joint replacement surgery.

Note that an example of the flow of the artificial knee joint replacement surgery has been described with reference to the flowchart shown in FIG. 7, but the present invention is not limited to this. FIG. 9 is a flowchart illustrating another example of the flow of the artificial knee joint replacement surgery.

Referring to FIG. 9, in the other example of the artificial knee joint replacement surgery, pretreatment (step S401) and installation of the reference marker 2 (step S402) are first performed. The specific content of steps S401 and S402 is the same as that of steps S301 and S302.

Then, post-treatment is performed (step S403). The specific content of step S403 is the same as that of the post-treatment of step S307. Then, the surgeon performs alignment measurement using the measuring instrument 1 (step S404). The specific content of step S404 is the same as that of the alignment measurement processing of step S305.

Then, if desired alignment has not been achieved (No, in step S405), the treatment of step S403 is again performed. On the other hand, if desired alignment has been achieved (Yes, in step S405), the surgeon performs treatment for installing the artificial knee joint component 200 in the patient 100 (step S406). The specific content of step S406 is the same as that of the treatment of step S308.

The above is the outline of the artificial knee joint replacement surgery. Hereinafter, the alignment measurement procedure (steps S305 and S404) will be described.

Figure 10:
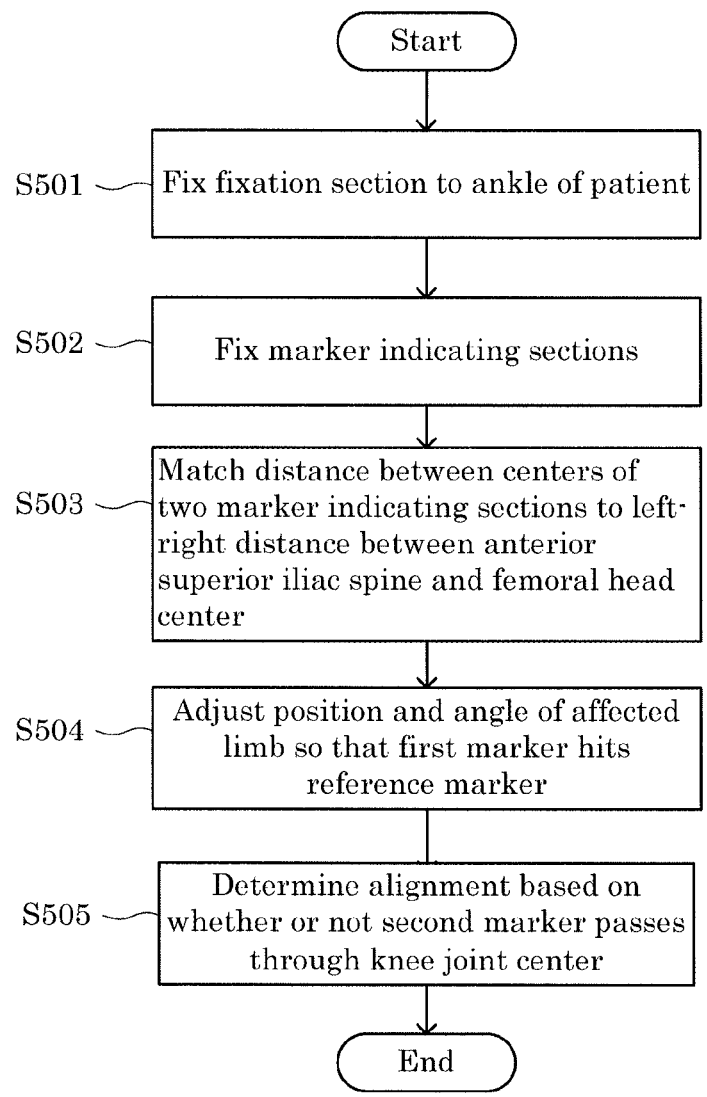
FIG. 10 is a flowchart illustrating an example of a flow of an alignment measurement procedure using the measuring instrument.

FIG. 10 is a flowchart illustrating an example of a flow of the alignment measurement procedure using the measuring instrument 1. Referring to FIG. 10, in the alignment measurement procedure, the surgeon first fixes the fixation section 4 to the ankle 114 of the patient 100 (step S501). Accordingly, the fixation section 4 is fixed to the ankle 114 while the pair of movable arms 8 and the fixed arm 7 of the fixation section 4 sandwich the ankle 114 of the patient 100.

Then, the surgeon fixes, to the fixation section 4, the movable base 5 to which the first marker indicating section 21 and the second marker indicating section 22 are attached (step S502). Then, the positions of the two marker indicating sections 21 and 22 are adjusted so that the distance between the centers of the light emitting surfaces 23 of the marker indicating sections 21 and 22 is equal to the preliminarily measured distance $\Delta X1$, in the left/right direction, between the anterior superior iliac spine 107 and the femoral head center P1 (step S503).

Then, the surgeon adjusts the position and the angle of the ankle 114 of the affected limb so that the first marker M1 (laser beam) emitted from the first marker indicating section 21 hits the reference marker 2 (step S504). Note that at this time, the first marker M1 is arranged so as to extend in the front/rear direction (direction in which the spine of the patient 100 extends).

Then, the surgeon checks whether or not the second marker M2 (laser beam) from the second marker indicating section 22 passes through the knee joint center P2 (step S505). If the second marker M2 passes through the knee joint center P2 of the artificial knee joint component 200, it is determined that the desired alignment has been achieved.

On the other hand, if the second marker M2 does not pass through the knee joint center P2 of the artificial knee joint component 200, it is determined that the desired alignment has not been achieved.

As described above, according to the measuring instrument 1 of the present embodiment, the patient 100 is subjected to X-ray photography, prior to the artificial knee joint replacement surgery. Accordingly, the relative positions of the anterior superior iliac spine 107 and the femoral head center P1 are measured with accuracy. Also, in the artificial knee joint replacement surgery, the anterior superior iliac spine 107 that can be viewed from the outside of the patient 100 is used as a mark, and the information regarding the above-described relative positions is used, so that the position of the femoral head center P1 that cannot be viewed is detected with accuracy. Also, the guide section 6 is installed so as to indicate the position of the detected femoral head center P1. Accordingly, the surgeon can correctly recognize the position of the femoral head center P1 of the patient 100 using the guide section 6 when performing the artificial knee joint replacement surgery. Therefore, the surgeon can perform, more accurately, the adjustment in alignment in which the position of the knee joint center P2 is adjusted using, for example, the femoral head center P1 of the patient 100, and the foot joint center P3 of the foot joint 105, which can be viewed from the outside of the patient 100, as references.

With this measure, it is possible to provide the measuring instrument 1 that can perform knee joint alignment measurement more accurately.

According to the measuring instrument 1, the guide section 6 is arranged based on the relative positions of the femoral head center P1 and the reference marker 2 fixed to the anterior superior iliac spine 107. According to the configuration, since the reference marker 2 is fixed to the anterior superior iliac spine 107, the surgeon can view the anterior superior iliac spine 107 serving as the reference area more clearly. Therefore, the surgeon can arrange the guide section 6 so that it indicate the position of the femoral head center P1 more correctly.

The anterior superior iliac spine 107 is a part that can easily be viewed by the surgeon from the outside of the patient 100. Accordingly, by setting the reference area to the anterior superior iliac spine 107, it is possible for the surgeon to easily view the reference area at the time of the artificial knee joint replacement surgery.

According to the measuring instrument 1, the second marker indicating section 22 indicates the second marker M2 that extends, when viewed from the outside of the patient 100, in the longitudinal direction of the patient 100 and passes through the femoral head center P1. According to the configuration, the second marker M2 can indicate the position of the femoral head center P1 more clearly. Furthermore, when the second marker M2 is arranged so as to pass through the foot joint center P3 of the foot joint 105 of the patient 100, it is possible for the surgeon to perform the adjustment in alignment of the artificial knee joint component 200 using this second marker M2 as a reference in a plan view. In this case, for example, the surgeon can perform the adjustment in alignment so that the second marker M2 and the knee joint center P2 overlap each other in a plan view.

According to the measuring instrument 1, the second marker M2 is a laser beam. According to this configuration, by adjusting the position, orientation, and the like of the second marker indicating section 22, it is easily possible to adjust the position of the second marker M2. Furthermore, it is possible to save the effort of carrying the second marker M2.

According to the measuring instrument 1, the guide section 6 is fixed to the patient via the fixation section 4. With this configuration, the guide section 6 can more reliably maintain the state of correctly indicating the position of the femoral head center P1.

According to the measuring instrument 1, the fixation section 4 is arranged at a position (position on the ankle 114) at which the fixation section 4 does not interfere with the artificial knee joint replacement surgery performed by the surgeon. Accordingly, the surgeon can more smoothly perform the artificial knee joint replacement surgery. Furthermore, by providing the first marker M1 indicating the reference area of the patient and the second marker M2 indicating the femoral head center P1 separately, it is possible to adjust the positions of the markers M1 and M2 independently. As a result, the position of the femoral head center P1 can be indicated to the surgeon with the markers M1 and M2 more correctly.

According to the measuring instrument 1, the first marker M1 and the second marker M2 are configured to be arranged parallel to each other. Furthermore, the distance, in the left/right direction, between the first marker M1 and the second marker M2 corresponds to the distance ΔX1, in the left/right direction, between the center of the anterior superior iliac spine 107 and the femoral head center P1. According to this configuration, the measuring instrument 1 can indicate the position of the femoral head center P1 using the markers M1 and M2 more correctly.

Second Embodiment

Figure 11:
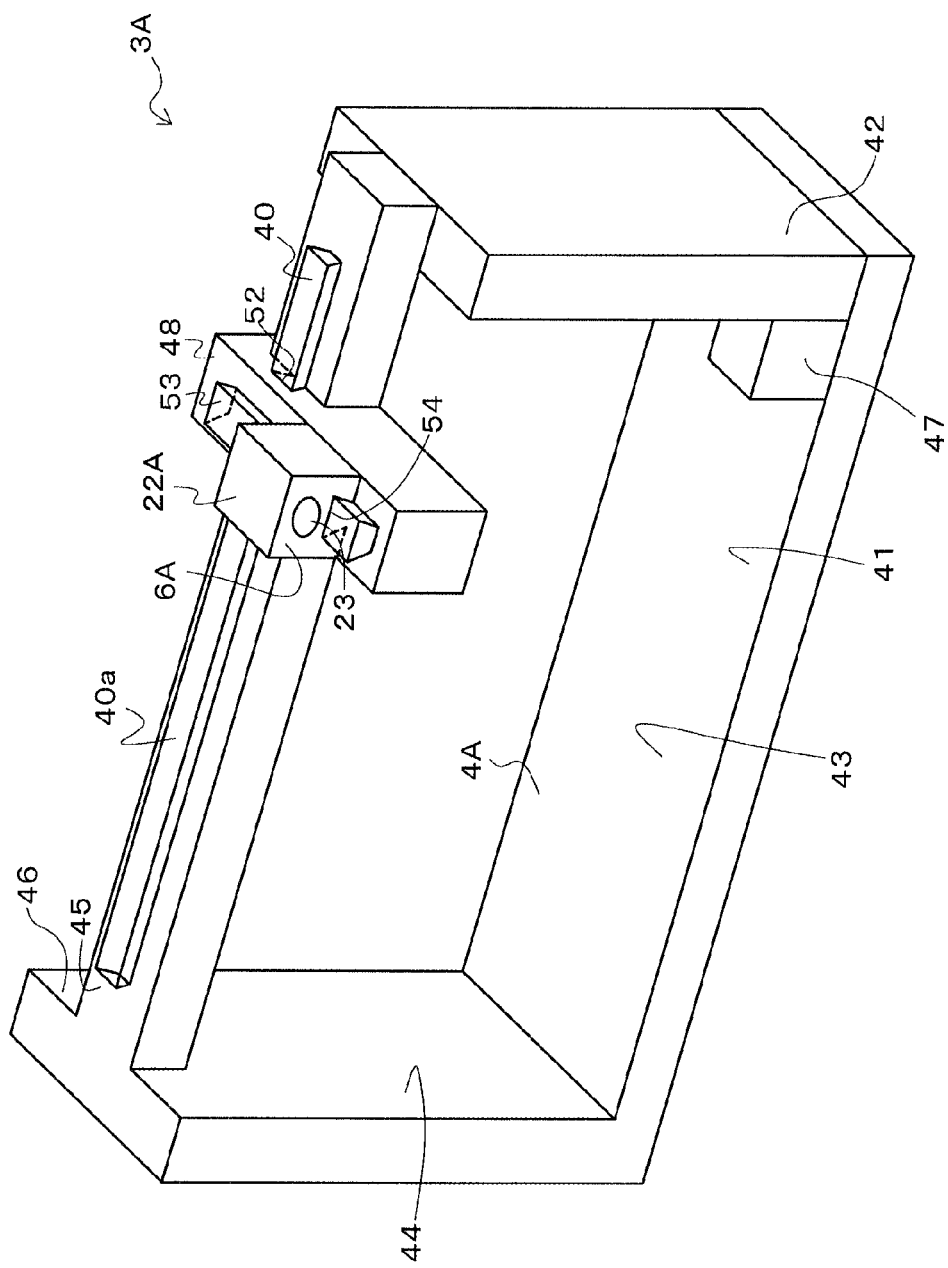
FIG. 11 is a schematic perspective view illustrating a guide unit according to a second embodiment.
Figure 12:
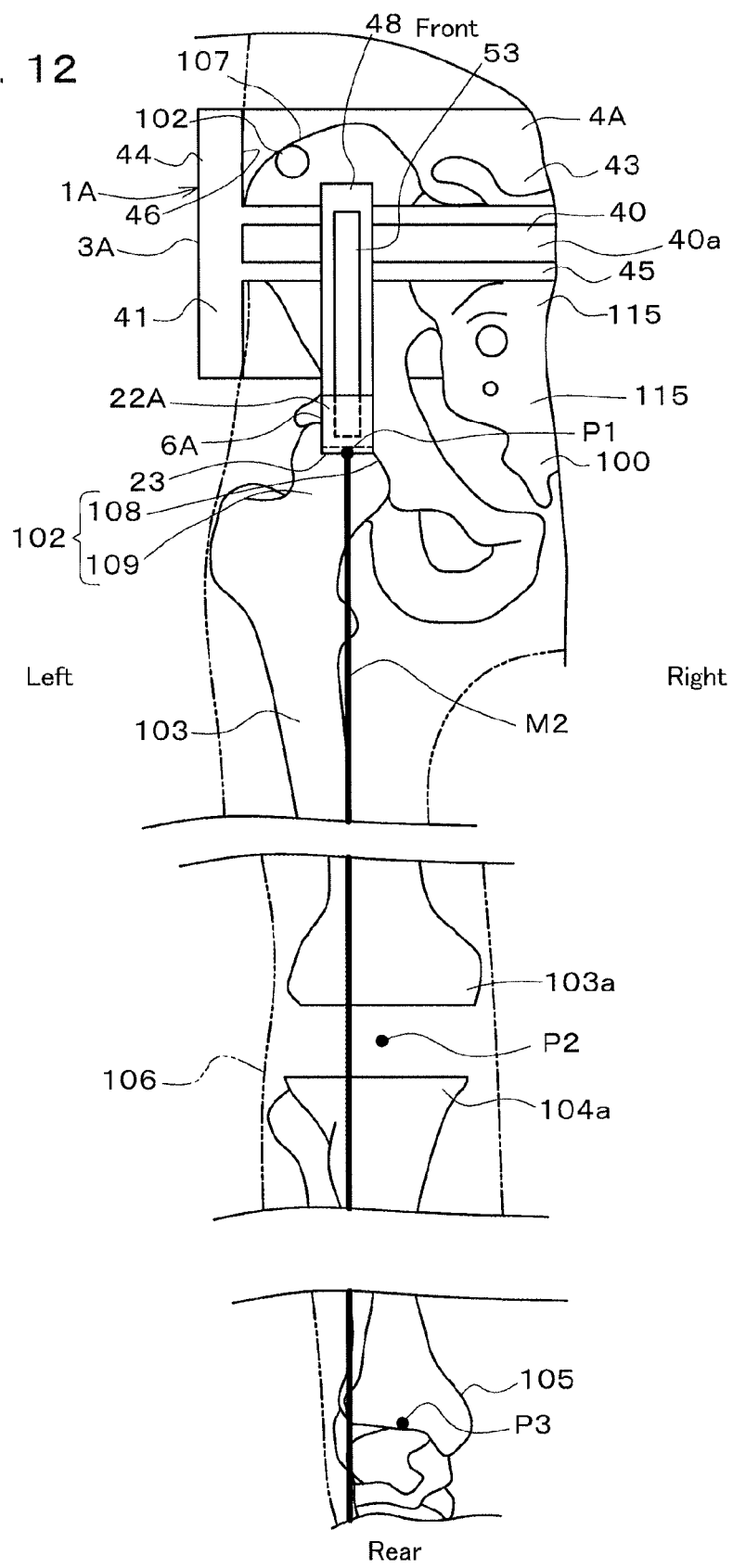

Hereinafter, a second embodiment of the present invention will be described. FIG. 11 is a perspective view schematically illustrating a guide unit 3A according to the second embodiment. FIG. 12 is a plan view illustrating a measuring instrument 1A and the like.

Figure 13:
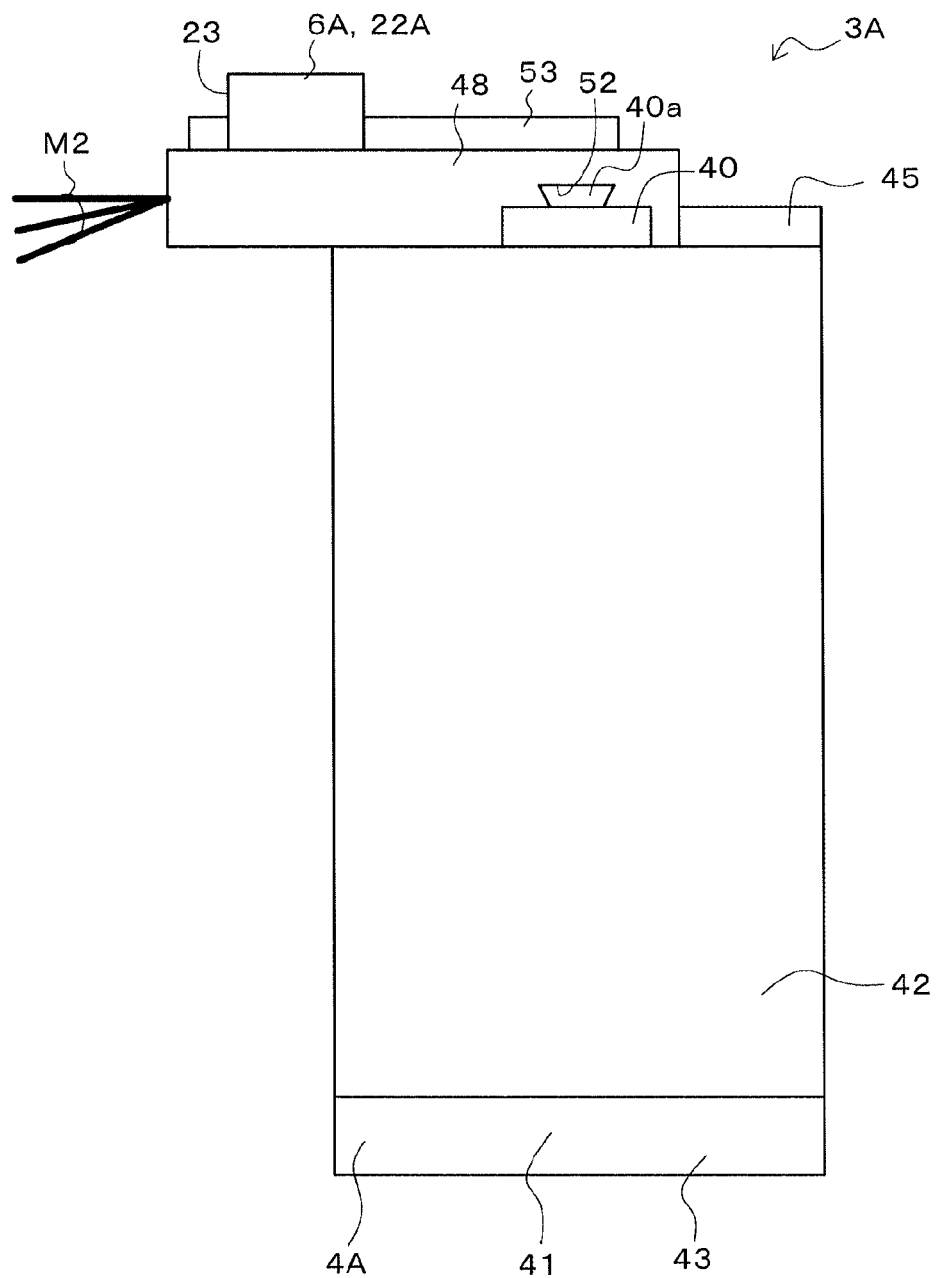
FIG. 13 is a side view illustrating the guide unit.

FIG. 13 is a side view illustrating the guide unit 3A Referring to FIGS. 11 to 13, in the second embodiment, a marker indicating section 22A of a guide section 6A is arranged at the femoral head center P1 of the patient 100. In the following, configurations different from that of the first embodiment will mainly be described, and the like reference numerals are given to the like configurations as those of the first embodiment and redundant description will be omitted.

The measuring instrument 1A has the reference marker 2 and the guide unit 3A.

In the present embodiment, the guide unit 3A is fixed to the pelvis 115 of the patient 100. This guide unit 3A is configured to indicate the position of the femoral head center P1.

The guide unit 3A has a fixation section 4A, a table mechanism 40, and the guide section 6A.

The fixation section 4A is a member that is fixed to the pelvis 115 of the patient 100, and is provided in order to fix the table mechanism 40 and the guide section 6A to the pelvis 115 of the patient 100. The fixation section 4A is rectangular frame shaped as a whole, and has a size through which the pelvis 115 of the patient 100 can pass.

The fixation section 4A has a frame 41 and a movable plate 42.

The frame 41 is provided as a backbone part of the fixation section 4A. The frame 41 is U-shaped as a whole.

The frame 41 has a bottom plate 43, a side plate 44, and an upper plate 45.

The bottom plate 43 has the shape of, for example, a rectangular flat plate, and the buttocks of the patient 100 are placed on the bottom plate 43. One end portion, in the left/right direction, of the bottom plate 43 supports the side plate 44. The side plate 44 is a rectangular plate-shaped portion extending in a direction orthogonal to the left/right direction, and is arranged on a side of the pelvis 115 of the patient 100. For example, the front end of the upper end part of the side plate 44 has a reference area portion 46.

The reference area portion 46 is provided as a portion that is arranged in the vicinity of the reference marker 2 at the time of alignment measurement. The upper end portion of the side plate 44 supports the upper plate 45. The upper plate 45 is a rectangular flat plate portion that extends in the left/right direction in an elongated manner. The upper plate 45 is supported by the side plate 44 and the movable plate 42.

The movable plate 42 is provided as a member that is displaceable with respect to the frame 41 in the left/right direction. The movable plate 42 is formed in a rectangular plate shape extending in a direction orthogonal to the left/right direction. The movable plate 42 is formed as a member separate from the frame 41, and is displaceable independently from the frame 41. The movable plate 42 and the frame 41 are made of metal for example, and a fixing member 47 such as a magnet is used for fixation of the movable plate 42 to, for example, the bottom plate 43 of the frame 41. Note that the configuration for fixing the movable plate 42 to the frame 41 is not limited to the configuration using the fixing member 47, and the present invention is not particularly limited in this respect.

At a position at which the movable plate 42 can cooperate with the side plate 44 to sandwich the pelvis 115 of the patient 100, the movable plate 42 is fixed to the frame 41 by the fixing member 47. Accordingly, the fixation section 4A is fixed to the pelvis 115 of the patient 100.

The guide unit 3A has the table mechanism 40 and the guide section 6A.

The table mechanism 40 is provided to support the guide section 6A, and to enable the position of the guide section 6A to be adjusted in the horizontal direction (left/right direction and front/rear direction).

The table mechanism 40 has the upper plate 45 and a movable member 48.

The upper plate 45 is a constituent component of the frame 41, and is a constituent component of the table mechanism 40. The upper surface of the upper plate 45 is flat, and is provided with a fixed rail 40a. The fixed rail 40a is formed with a straight line shape and extends in the left/right direction. Note that, hereinafter, the state in which the fixation section 4A is fixed to the pelvis 115 is also referred to simply as the fixed state of the fixation section 4A. The fixed rail 40a has a trapezoidal cross-section that is orthogonal to the longitudinal direction of the fixed rail 40a. In other words, in the fixed state of the fixation section 4A, the fixed rail 40a has an inverse tapered shape such that width of the fixed rail 40a in the front/rear direction increases toward the upper side from the frame 41. The movable member 48 is connected to the fixed rail 40a.

The movable member 48 is provided as a section that supports the guide section 6A, and is displaceable with respect to the fixation section 4A in the left/right direction. The movable member 48 is an elongated bar-like member that extends in the front/rear direction.

The movable member 48 has a lower rail 52 and an upper rail 53.

The lower rail 52 is slidably connected to the fixed rail 40a. The lower rail 52 is a recess-like part formed on the lower surface of the movable member 48, and extends in the left/right direction. The lower rail 52 has a shape that corresponds to the shape of the fixed rail 40a, and is slidable relative to the fixation section 4A in the left/right direction. Note that the movable member 48 may be fixable to the lower rail 52 using a fixing member that is not shown. The upper rail 53 is formed on the upper surface of a movable base 5A.

The upper rail 53 is provided in order to hold the guide section 6A The upper rail 53 is a protruding section formed on the upper surface of the movable base 5A, and extends in the front/rear direction. The upper rail 53 has an inverse tapered shape such that width of the upper rail 53 in the left/right direction increases toward the upper side. The upper rail 53 supports the guide section 6A.

The guide section 6A has the second marker indicating section 22A.

The second marker indicating section 22A has a light emitting surface 23 that faces the foot joint 105 (rearward) of the patient 100, and emits a laser beam from this light emitting surface 23. The second marker indicating section 22A emits a laser beam toward the patient 100 in the shape of a fan in a side view.

A lower rail 54 of the second marker indicating section 22A is provided as a section that is connected to the upper rail 53, and is configured to enable the second marker indicating section 22A to slide relative to the movable member 48 in the front/rear direction. The lower rail 54 is a recess-like part formed on the lower surface of the second marker indicating section 22A, and extends in the front/rear direction. The lower rail 54 has a shape that corresponds to the shape of the upper rail 53, and is fitted to the upper rail 53. Note that the second marker indicating section 22A may be fixable to the upper rail 53 using a fixing member that is not shown.

The second marker indicating section 22A is arranged at the femoral head center P1, based on the preliminarily measured relative positional relationship between the anterior superior iliac spine 107 and the femoral head center P1. The second marker indicating section 22A is provided in order to indicate the linear second marker M2 that indicates the position of the femoral head center P1 of the patient 100. The second marker M2 is emitted from the second marker indicating section 22A arranged at the position of the femoral head center P1 so as to extend in the longitudinal direction of the patient 100 (front/rear direction) in a plan view from the outside of the patient 100.

Accordingly, the second marker M2 can be emitted so as to pass through the foot joint center P3 of the foot joint 105 in a plan view.

The above is a schematic configuration of the measuring instrument 1A The following will describe the outline of the flow of the alignment measurement procedure (steps S305 and S404) using the measuring instrument 1A.

Figure 14:
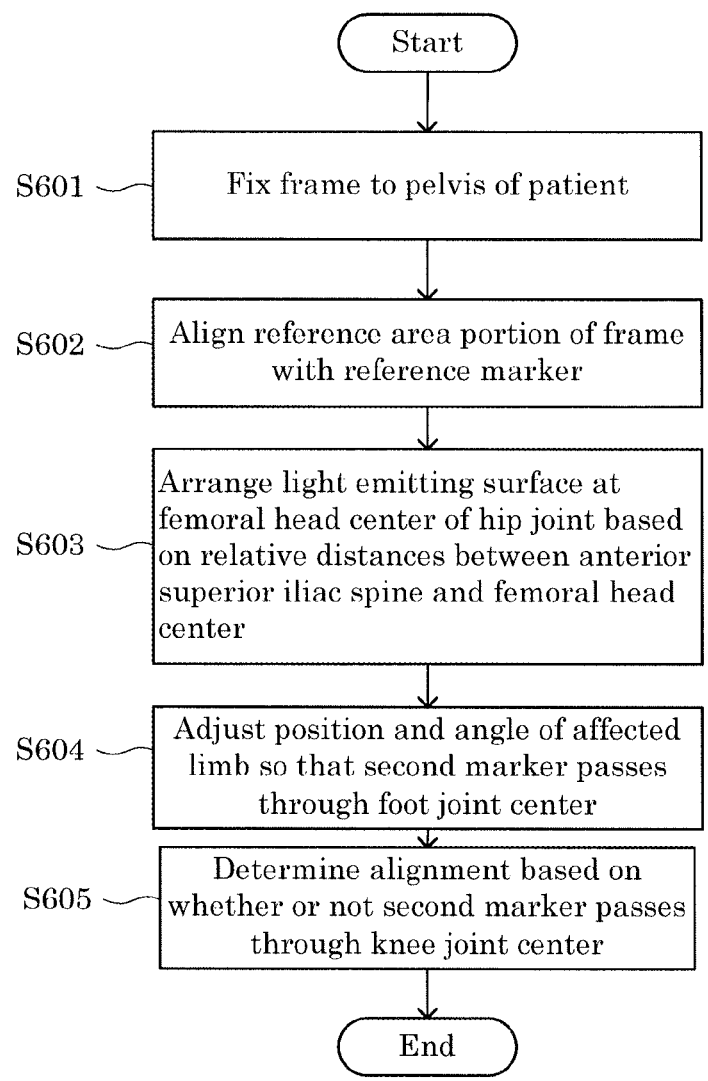
FIG. 14 is a flowchart illustrating an alignment measurement procedure using the measuring instrument.

FIG. 14 is a flowchart illustrating the alignment measurement procedure using the measuring instrument 1A. Referring to FIG. 14, in this alignment measurement procedure, the surgeon first fixes the fixation section 4A to the pelvis 115 of the patient 100 (step S601). Accordingly, the pelvis 115 of the patient 100 is sandwiched between the side plate 44 and the movable plate 42 of the fixation section 4A. Accordingly, the fixation section 4A is fixed to the pelvis 115.

Then, the surgeon aligns the reference area portion 46 of the side plate 44 of the frame 41 with the reference marker 2 (step S602). Accordingly, the position of the reference area portion 46 substantially matches the position of the reference marker 2.

Then, the surgeon adjusts the position of the second marker indicating section 22A so that the relative positions of the anterior superior iliac spine 107 and the femoral head center P1 that were measured in the preoperative examination match the relative positions of the reference marker 2 and the light emitting surface 23 of the second marker indicating section 22A (step S603). At this time, the surgeon makes position adjustment by displacing the second marker indicating section 22A in the left/right direction and the front/rear direction. Accordingly, the light emitting surface 23 is arranged at the femoral head center P1.

Then, the surgeon adjusts the position and the angle of the limb of the patient 100 so that, in a plan view, the second marker M2 (laser beam) emitted from the second marker indicating section 22A passes through the foot joint center P3 of the foot joint 105 (step S604).

Then, the surgeon checks whether or not the second marker M2 from the second marker indicating section 22 passes through the knee joint center P2 (step S605). At this time, if the second marker M2 passes through the knee joint center P2 of the artificial knee joint component 200, desired alignment has been achieved. On the other hand, if the second marker M2 does not pass through the knee joint center P2 in a plan view, desired alignment has not been achieved.

According to the measuring instrument 1A, the second marker indicating section 22A is arranged at the femoral head center P1. Accordingly, the second marker indicating section 22A itself functions as a mark indicating the femoral head center P1. The surgeon can thus view the position of the femoral head center P1 more clearly.

Figure 15:
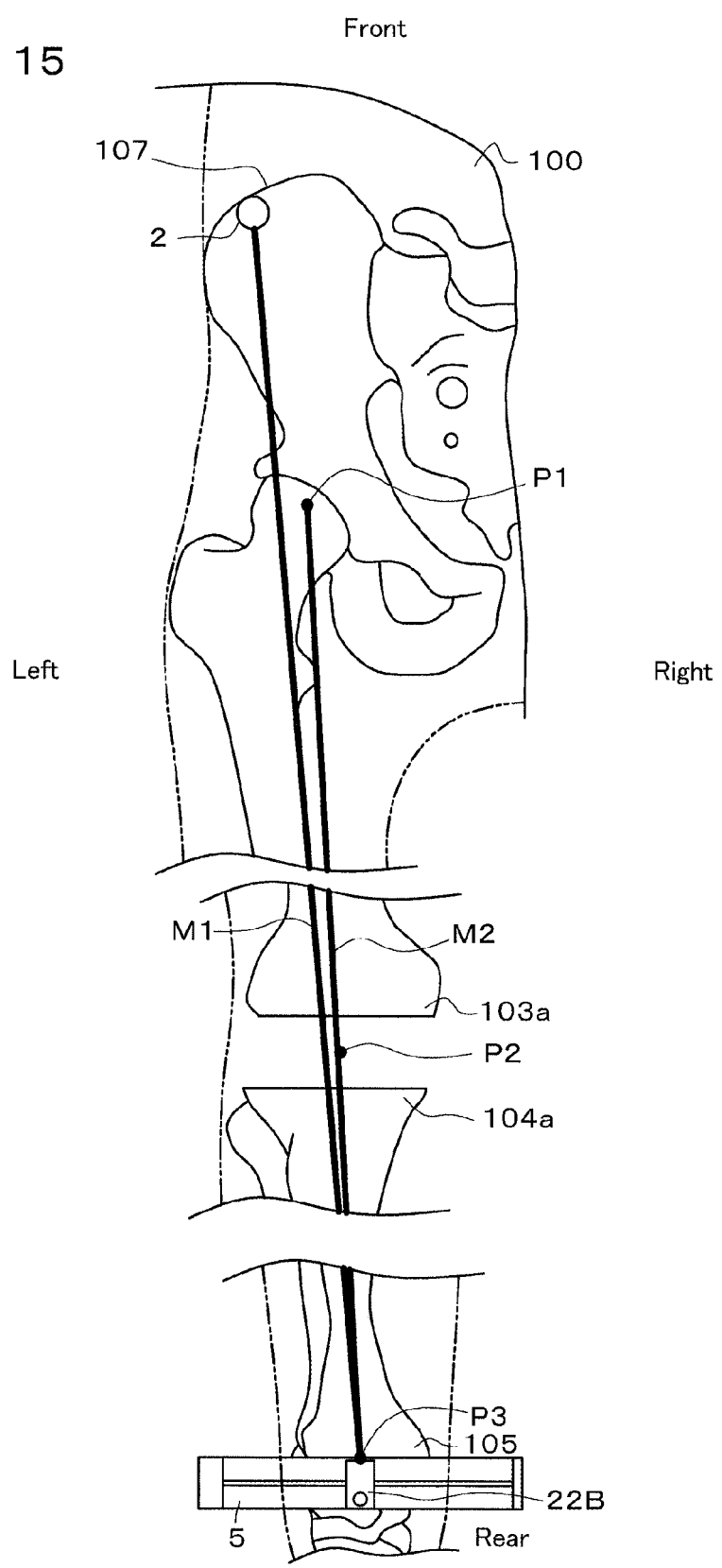
FIG. 15 is a schematic plan view illustrating a main part according to a modification.

The embodiments of the present invention have been described so far, but the present invention is not limited to the foregoing embodiments and various modifications are possible within the recitation of the Claims. For example, the following modifications are possible:

(1) Although, for example, the first embodiment has described, as an example, an aspect in which two marker indicating sections are used, there is no limitation to this. For example, as shown in FIG. 15, a single marker indicating section 22B may be used. The marker indicating section 22B is configured to emit two linear laser beams in a plan view. The angle between the two laser beams is determined by preoperative planning, and is adjusted so that, when one of the laser beams that serves as the first marker M1 is emitted from the foot joint center P3 to the reference marker 2, the other laser beam that serves as the second marker M2 is emitted from the foot joint center P3 to the femoral head center P1. Similarly to the other embodiments, the laser beam is linear in a plan view, and is emitted in the shape of a fan in a side view. The surgeon can perform adjustment in alignment so that the laser beam serving as the second marker M2 overlaps the knee joint center P2.

(2) The foregoing embodiments have described, as an example, an aspect in which laser light sources are used as the first marker indicating section and the second marker indicating section. However, there is no limitation to this. For example, metal bars or threads may be used as the marker indicating sections. In this case, the metal bar or thread itself functions as a marker. If the marker is a metal bar, with a simple configuration in which the metal bar is arranged so as to overlap the femoral head center in a plan view, it is possible for the marker to indicate the position of the femoral head center. If the marker is a thread, with a simple configuration in which the thread is extended near the body of the patient, it is possible for the marker to indicate the position of the femoral head center.

(3) The foregoing embodiments have described, as an example, an aspect in which an anterior superior iliac spine is used as a reference area of a patient. However, there is no limitation to this. The reference area of the patient may be any position as long as it can be easily viewed by a surgeon at the time of artificial knee joint replacement surgery, and may be, for example, an anterior inferior iliac spine or the like.

(4) Note that, although the various embodiments of the present invention have been described so far, it is sufficient for the measuring instrument for use in artificial knee joint replacement surgery of the present invention to include a guide section, and there is no limitation on the other configurations.

INDUSTRIAL APPLICABILITY

The present invention is widely applicable as a measuring instrument for use in artificial knee joint replacement surgery, which is used in surgery for replacing a knee joint of a patient with an artificial knee joint.

DESCRIPTIONS OF REFERENCE NUMERALS 1, 1A Measuring instrument for use in artificial knee joint replacement surgery
2 Reference marker
4, 4A Fixation section
6, 6A Guide section
21 First marker indicating section
22, 22A, 22B, 22C Second marker indicating section (marker indicating section)
100 Patient
102 Hip joint
107 Anterior superior iliac spine (reference area)
114 Ankle
115 Pelvis
M1, M1C First marker
M2, M1C Second marker (femoral head center marker)
P1 Femoral head center

The invention claimed is:

1. A measuring instrument for use in artificial knee joint replacement surgery, comprising:
   a guide section for indicating, from the outside of a patient's body without incision of the patient's body, a position of a femoral head center of a hip joint of the patient, and
   a fixation section for fixing the guide section to the patient;
   wherein the fixation section is configured to be fixed to an ankle of the patient;
   wherein the guide section is configured to indicate the position of the femoral head center while being arranged based on preliminarily measured relative positions of a reference area and the femoral head center of the patient, the reference area being viewable from the outside of the patient's body without incision of the patient's body;
   wherein the guide section includes a first marker indicating section that indicates a first marker that is shaped as a straight line that passes through the reference area of the patient, and a second marker indicating section that indicates a second marker that is shaped as a straight line;
   wherein the second marker is a femoral head center marker that extends, when viewed from the outside of the patient, in the longitudinal direction of the patient and passes through the femoral head center.

2. The measuring instrument for use in artificial knee joint replacement surgery according to claim 1,
   wherein the guide section is arranged based on relative positions of a reference marker that is fixed to the reference area, and the femoral head center.

3. The measuring instrument for use in artificial knee joint replacement surgery according to claim 1,
   wherein the reference area includes an iliac spine of the patient.

4. The measuring instrument for use in artificial knee joint replacement surgery according to claim 1,
   wherein the guide section includes a marker indicating section, and
   the marker indicating section indicates the femoral head center marker that extends, when viewed from the outside of the patient, in the longitudinal direction of the patient and passes through the femoral head center.

5. The measuring instrument for use in artificial knee joint replacement surgery according to claim 1,
   wherein the femoral head center marker is a laser beam, a metal bar, or a thread.

6. The measuring instrument for use in artificial knee joint replacement surgery according to claim 1,
   wherein the first marker and the second marker are configured to be arranged parallel to each other, and
   a distance between the first marker and the second marker in a left/right direction of the patient corresponds to a distance between the reference area and the femoral head center in the left/right direction.

7. A method of using a measuring instrument for use in artificial knee joint replacement surgery, the method comprising:
   taking an x-ray photograph of a leg of a patient, wherein the x-ray photograph includes at least a femoral head center and a reference area being viewable from outside of the patient without incision of the patient's body;
   determining a distance between the femoral head center and the reference area of the patient based on the x-ray photograph;
   positioning a guide section of the measuring instrument to the leg of the patient based on a preliminary measured relative position of the femoral head center and a preliminary measured relative position of the reference area of the patient, without incision of the patient's body based on the determined distance; and
   determining a position of the femoral head center using the measuring instrument based on a preliminarily measured relative position of the reference area and the preliminarily measured relative position of the femoral head center of the patient.

* * * * *